(12) United States Patent
Miller

(10) Patent No.: US 8,645,424 B2
(45) Date of Patent: Feb. 4, 2014

(54) SYSTEM FOR ELECTRONICALLY RECORDING AND SHARING MEDICAL INFORMATION

(76) Inventor: Sam Stanley Miller, San Antonio, TX (US)

(*) Notice: Subject to any disclaimer, the term of this patent is extended or adjusted under 35 U.S.C. 154(b) by 623 days.

(21) Appl. No.: 12/499,592

(22) Filed: Jul. 8, 2009

(65) Prior Publication Data

US 2009/0276463 A1 Nov. 5, 2009

Related U.S. Application Data

(63) Continuation-in-part of application No. 12/339,748, filed on Dec. 19, 2008, now abandoned.

(60) Provisional application No. 61/008,326, filed on Dec. 19, 2007.

(51) Int. Cl.
*G06F 7/00* (2006.01)
*G06F 17/30* (2006.01)

(52) U.S. Cl.
USPC .......................... 707/783; 707/781; 707/782

(58) Field of Classification Search
USPC ................. 707/607, 608, 609, 781, 782, 783
See application file for complete search history.

(56) References Cited

U.S. PATENT DOCUMENTS

| | | | |
|---|---|---|---|
| 5,772,585 A | 6/1998 | Lavin et al. | |
| 5,832,450 A | 11/1998 | Myers et al. | |

(Continued)

FOREIGN PATENT DOCUMENTS

| | | |
|---|---|---|
| JP | 03337864 | 11/2003 |
| WO | 0028437 | 5/2000 |

(Continued)

OTHER PUBLICATIONS

Requirements for EHR Systems Providing Source for Clinical Research, Electronic Health Records/Clinical Research, EHR/CR User Requirements Document, EHR/CR Functional Profile Working Group, eClinical Forum, PhRMA EDC/eSource Task Force, Draft for Comment Nov. 1, 2007, Nov. 7, 2007, p. 1-29.

(Continued)

*Primary Examiner* — Etienne Leroux
*Assistant Examiner* — Jared Bibbee
(74) *Attorney, Agent, or Firm* — Raymond R. Ferrera; Adams and Reese LLP

(57) ABSTRACT

A system for electronically recording and sharing medical data is provided, the system comprising an electronic source document, wherein the electronic source document comprises a database. In one particular embodiment, the medical data comprise clinical study data, and in another the medical data comprise patient specific data. In some embodiments, the system includes means for defining data parameters and storing the data parameters within the electronic source document, as well as a browser-based means for entering data into the electronic source document and storing the data therein. In a further embodiment, the system comprises means for one or more users of the system to view stored data. In a still further embodiment, means for one or more users to amend data stored in the electronic source document is provided, and in yet another embodiment the system comprises means for creating and maintaining an audit trail when one or more of the users amends data stored in the electronic source document. In other embodiments, the system further comprises an application specific navigation tool; in some embodiments, the application specific tool comprises a graphical user interface. Appropriate methods of using the system are also provided.

16 Claims, 1 Drawing Sheet

(56) References Cited

U.S. PATENT DOCUMENTS

| | | | |
|---|---|---|---|
| 5,845,255 A | 12/1998 | Mayaud | |
| 5,924,074 A | 7/1999 | Evans | |
| 5,991,731 A | 11/1999 | Colon et al. | |
| 6,108,635 A | 8/2000 | Herren et al. | |
| 6,149,440 A | 11/2000 | Clark et al. | |
| 6,168,563 B1 | 1/2001 | Brown | |
| 6,171,112 B1 | 1/2001 | Clark et al. | |
| 6,192,345 B1 | 2/2001 | Chicorel | |
| 6,226,745 B1 | 5/2001 | Wiederhold | |
| 6,263,330 B1 | 7/2001 | Bessette | |
| 6,304,848 B1 | 10/2001 | Singer | |
| 6,341,267 B1 | 1/2002 | Taub | |
| 6,347,329 B1 | 2/2002 | Evans | |
| 6,363,393 B1 | 3/2002 | Ribitzky | |
| 6,381,577 B1 | 4/2002 | Brown | |
| 6,496,827 B2 | 12/2002 | Kozam et al. | |
| 6,529,876 B1 | 3/2003 | Dart et al. | |
| 6,556,999 B1 | 4/2003 | Kloos et al. | |
| 6,587,830 B2 | 7/2003 | Singer | |
| 6,602,469 B1 | 8/2003 | Maus et al. | |
| 6,611,846 B1 | 8/2003 | Stoodley | |
| 6,681,003 B2 | 1/2004 | Linder et al. | |
| 6,684,276 B2 | 1/2004 | Walker et al. | |
| 6,687,190 B2 | 2/2004 | Momich et al. | |
| 6,723,051 B2 | 4/2004 | Davidson et al. | |
| 6,734,886 B1 | 5/2004 | Hagan et al. | |
| 6,740,038 B2 | 5/2004 | Davidson et al. | |
| 6,770,029 B2 | 8/2004 | Iliff | |
| 6,789,091 B2 | 9/2004 | Gogolak | |
| 6,792,574 B1 | 9/2004 | Sugiyama | |
| 6,820,235 B1 | 11/2004 | Bleicher et al. | |
| 6,874,085 B1 | 3/2005 | Koo et al. | |
| 6,875,020 B2 | 4/2005 | Niddrie et al. | |
| 6,904,434 B1 | 6/2005 | Wallach et al. | |
| 6,925,599 B2 | 8/2005 | Wood | |
| 6,985,846 B1 | 1/2006 | Dunlavey | |
| 7,085,757 B2 | 8/2006 | Dettinger et al. | |
| 7,089,247 B2 | 8/2006 | Kloos et al. | |
| 7,092,891 B2 | 8/2006 | Maus et al. | |
| 7,104,958 B2 | 9/2006 | Crutchfield et al. | |
| 7,165,062 B2 | 1/2007 | O'Rourke | |
| 7,174,335 B2 | 2/2007 | Kameda | |
| 7,230,529 B2 | 6/2007 | Ketcherside, Jr. et al. | |
| 7,233,906 B1 | 6/2007 | Aghili et al. | |
| 7,251,609 B1* | 7/2007 | McAlindon et al. | 705/3 |
| 7,251,610 B2 | 7/2007 | Alban et al. | |
| 7,269,578 B2 | 9/2007 | Sweeney | |
| 7,275,220 B2 | 9/2007 | Brummel et al. | |
| 7,349,947 B1 | 3/2008 | Slage et al. | |
| 7,395,215 B2 | 7/2008 | Grushka | |
| 7,412,658 B2 | 8/2008 | Gilboa | |
| 7,424,437 B2 | 9/2008 | Maus et al. | |
| 7,596,541 B2 | 9/2009 | deVries et al. | |
| 2001/0034617 A1* | 10/2001 | Kimata | 705/3 |
| 2001/0051882 A1 | 12/2001 | Murphy et al. | |
| 2002/0010552 A1 | 1/2002 | Rienhoff, Jr. et al. | |
| 2002/0010595 A1 | 1/2002 | Kapp | |
| 2003/0037054 A1 | 2/2003 | Dutta et al. | |
| 2003/0097291 A1 | 5/2003 | Freedman | |
| 2003/0222918 A1* | 12/2003 | Coulthard | 345/780 |
| 2004/0034550 A1 | 2/2004 | Menschik et al. | |
| 2004/0068521 A1 | 4/2004 | Haacke et al. | |
| 2004/0230592 A1 | 11/2004 | Fischer et al. | |
| 2005/0010451 A1 | 1/2005 | Marks et al. | |
| 2005/0038342 A1 | 2/2005 | Mozayeni et al. | |
| 2005/0165627 A1* | 7/2005 | Fotsch et al. | 705/3 |
| 2006/0184422 A1* | 8/2006 | Cooper et al. | 705/16 |
| 2006/0195269 A1 | 8/2006 | Yeatman et al. | |
| 2006/0229909 A1 | 10/2006 | Kaila et al. | |
| 2006/0259783 A1 | 11/2006 | Work et al. | |
| 2007/0067210 A1 | 3/2007 | Rishell et al. | |
| 2007/0078685 A1 | 4/2007 | Dettinger et al. | |
| 2007/0078687 A1 | 4/2007 | Dettinger et al. | |
| 2007/0100663 A1 | 5/2007 | Zammit | |
| 2007/0168242 A1 | 7/2007 | Brown | |
| 2007/0179778 A1* | 8/2007 | Gong et al. | 704/9 |
| 2007/0185751 A1 | 8/2007 | Dempers | |
| 2007/0185826 A1* | 8/2007 | Brice et al. | 707/1 |
| 2007/0208750 A1 | 9/2007 | Carmeli et al. | |
| 2007/0214012 A1 | 9/2007 | Loew et al. | |
| 2007/0250779 A1* | 10/2007 | Wallach et al. | 715/740 |
| 2008/0086337 A1* | 4/2008 | Soon-Shiong | 705/3 |
| 2008/0154640 A1 | 6/2008 | DeMeyer et al. | |
| 2008/0275738 A1* | 11/2008 | Shillingburg | 705/3 |
| 2009/0204421 A1* | 8/2009 | Guimaraes | 705/2 |
| 2011/0029488 A1* | 2/2011 | Fuerst et al. | 707/636 |

FOREIGN PATENT DOCUMENTS

| | | |
|---|---|---|
| WO | 0217211 | 2/2002 |
| WO | 0226118 A2 | 4/2002 |
| WO | 02101496 | 12/2002 |
| WO | 2004038560 | 5/2004 |
| WO | 2004102333 | 11/2004 |
| WO | 2008073359 | 6/2008 |
| WO | 2008086311 | 7/2008 |

OTHER PUBLICATIONS

General Principles of Software Validation; Final Guidance for Industry and FDA Staff, U.S. Department of Health and Human Services, Food and Drug Administration, Center for Devices and Radiological Health, Center for Biologics Evaluation and Research, Jan. 11, 2002, p. i-iv and 1-43.
Inspections, Compliance, Enforcement, and Criminal Investigations, Attachment A, Computerized Systems, Department of Health and Human Services, Food and Drug Administration, FDA Home> Inspections, Compliance, Enforcement, and Criminal Investigations> Enforcement Actions> Bioresearch Monitoring, Page Last Updated: May 6, 2009, p. 1-3.
CFR—Code of Federal Regulations Title 21, Department of Health and Human Services, Food and Drug Administration, FDA Home> Medical Devices> Databases, Page Last Updated: Apr. 1, 2008, p. 1.
Critical Path Opportunities Initiated During 2006, Science & Research, Department of Health and Human Services, Food and Drug Administration, FDA Home> Science & Research> Science and Research Special Topics> Critical Path Initiative, Page Last Updated: Jun. 18, 2009, p. 1-17.
FDA, NCI, and CRIX International to Collaborate on FIREBIRD Pilot, News, Memorandum of Agreement Establishes Public-Private Partnership to Ensure Successful Pilot, © 2007 CRIX International, p. 1-2.
Inspections, Compliance, Enforcement, and Criminal Investigations, Electronic Records: Electronic Signature Certification, Department of Health and Human Services, Food and Drug Administration, FDA Home> Inspections, Compliance, Enforcement, and Criminal Investigations> Inspections> Field Management Directives, Page Last Updated: Apr. 30, 2009, p. 1-3.
Better Medicines, Improving Safety with Every Step, Drug Information Association 45th Annual Meeting, Jun. 21-25, 2009, p. 1-3.
Paul Bleicher, Michael Owings, Kenneth O'Brrien, Comments Submission: Dec. 21, 2001, p. 1-3.
Firebird, National Cancer Institute, U.S. National Institutes of Health, Home >> Projects >> FIREBIRD, Last modified Sep. 18, 2006 11:14 AM, p. 1-2.
Kimberly A. Trautman, Medical Devices, Presentation: Quality System Regulation 21 CFR 820—Basic Introduction, Department of Health and Human Services, Food and Drug Administration, FDA Home> Medical Devices> Resources for You (Medical Devices)> Industry (Medical Devices), Page Last Updated: Apr. 30, 2009, p. 1-14.
Study Portal, Investigator & Enterprise-Wide Portal Solutions, Case Study-Site Activator, ePharmaSolutions, p. 1.
Jules Mitchel, Joon You, Yong Joong Kim, Ronald Nardi, Linda Cheng, Seymour Fein, Amy Lau Clinical Trial Data Integrity, Applied Clinical Trials, © 2007 Advanstar Communications, Mar. 2, 2003, p. 1-6.

(56) References Cited

OTHER PUBLICATIONS

Clinical Trials Resource—Consortia Step-By-Step, Step 2: Conducting a Cancer Prevention Clinical Trial Essential Documents, National Cancer Institute, U.S. National Institutes of Health, Division of Cancer Prevention, p. 1-5.
Suzanne Bishop, Unraveling the eSource—Industry-wide standards for electronic patient data have long felt like buried treasure. Companies today are getting closer—by way of a tangled map., Pharmaceutical Executive, Nov. 1, 2006, p. 1-6.
Ed Helton, Sally Cassells, and Dave Iberson-Hurst, Why Clinical Development Teams Should Care about Data Standards—Part I: An Introduction to the CDISC Operational Data Model (ODM) (audio seminar), May 2, 2006, p. 1-2.
The Future Vision of Electronic Health Records as eSource for Clinical Research, eClinical / PhRMA EDC/eSource Taskforce Joint Team, First Release, Version 1.0, Sep. 14, 2006, p. 1-41.
Electronic Case Report Form Submission; Notice of Pilot Project, From the Federal Register Online via GPO Access [wais.access.gpo.gov], Department of Health and Human Services, Food and Drug Administration, vol. 72, No. 48, Mar. 13, 2007, p. 11370-11371.
Rebecca D. Kush, Bron Kisler, CDISC—Progress, Benefits and Global Uptake, Clinical Data Interchange Standards Consortium, MD Anderson & UT Health, Science Center (Houston, Tx), Jun. 27, 2007, p. 1-66.
ATMs for healthcare, Copyright © 1997-2008 Data Conversion Laboratory, Inc., DCLnews editorial, Apr. 15, 2004, p. 1-4.
Deborah Grider, Robin Linker, Susan Thurston, Stephen Levinson, The problem with EHRs and coding, Medical Economics, Apr. 3, 2009, p. 1-11.
Human health and the IP system: Innovation, access and public welfare, Working draft: An overview of the issues, Sep. 2007, p. 1-25.
Elaine Rubin, Danielle Lazar, Nick Gaich, and David Haray, The Clinical Trials Landscape: Limitations, Strengths, and Promise, © 2007 Association of Academic Health Care, p. 1-12.
Elodia Cole, Etta D. Pisano, Gregory J. Clary, Donglin Zeng, Marcia Koomen, Cherie M. Kuzmiak, Bo Kyoung Seo, Yeonhee Lee, Dag Pavic, A compartive study of mobile electronic data entry system for clinical trials data collection, University of North Carolina, Lineberger Comprehensive Cancer Center, CB#7515, Radiology Research Labs, Oct. 17, 2005, p. 1-16.
Adobe electronic forms for clinical development, © 2007 Adobe Systems, Incorporated, p. 1-5.
Kevin Berg, Noah Yosha, An Electronic Paradigm: A Look into the Changing World of Clinical Trials, FAC/Equities, A Division of First Albany Corporation, Industry Report, p. 1-32.
Auditing Electronic data capture in clinical trials (EDC)—The auditor's view, p. 1-18.
Electronic Medical Records in Australia and Clinical Trials, Briefing Document prepared by eMedical Record Australian Pharmaceutical Industry Working Group (A collaboration between the ARCS Clinical Quality & Compliance Education Sub-committee and the Pharmaceutical Industry Council R&D Taskforce), Version 3.0, Mar. 6, 2008, p. 1-9.
Electronic Health Records/Clinical Research, EHR/CR Functional Profile, Global Project and Profile Description Document (Working Document), EHR/CR Functional Profile Working Group, Health Level 7 and EuroRec, Version 0.8, Aug. 2007, p. 1-14.
Understanding Evolving Standards for Clinical Data Management and Regulatory Submissions, XML and Pharmaceutical Data Management Summit 2003, Date of snapshot: May 20, 2003. From: http://www.cptpharma.org/ Sep. 23-24, 2003 Philadelphia, Pennsylvania, p. 1-8.
Clinical Trial Software for Electronic Data Capture, OpenClinica, p. 1.
Steven P. Schwartz, Electronic Health Records in Clinical Trials and Research, p. 1-19.
Winston Salem, Clinical Ink Unveils New Web Site, Version 1.0 of its eSource Solution for Electronic Data Capture, Datasci Patent License Key to Growth and Success, PRNewswire, © Thomson Reuters 2008, Jan. 15, 2008, p. 1-3.
John Hill talks tablets, Clinical Ink automates clinical trials using tablet PCs, May 6, 2008, p. 1-2.
CTMR Investigator Source Document Software®, Providing technology resources for the Clinical Trial Industry, Clinical Trial Management Resources, LLC, p. 1.
Anne Tompkins, Data Management, Jan. 29, 2007, p. 1-22.
Clinical Trials, Laegemiddel Styrelsen, Danish Medicine Agency, Sep. 19, 2008, p. 1-2.
Electronic Data in Clinical Trials, CHI Conferences > Electronic Data in Clinical Trials, Sep. 21, 2008, p. 1-2.
Guidance for Industry Computerized Systems Used in Clinical Investigations, U.S. Department of Health and Human Services Food and Drug Administration (FDA), Office of the Commissioner (OC), FDA.com Information Portal, May 2007, p. 1-10.
A. El Fadly, C. Daniel, C. Bousquet, T. Dart, P-Y. Lastic, Electronic Healthcare Record and Clinical Research in Cardiovascular Radiology HL7 CDA and CDISC ODM Interoperability, p. 1-7.
Important Aspects of GCP in Source Documentation, p. 1-5.
Liora Alschuler, Rebecca Kush, Landen Bain, Improving Data Collection for Patient Care and Clinical Trials, Science Home>Science Careers>Career Magazine>Previous Issues>2004>Mar. 26, 2004>Alschuler, Mar. 26, 2004, p. 1-2.
Stella Tsai, Chicquita Hatten, Linda R. Eckert, Melissa A. Brown, Bei Wang, Electronic Regulatory Document Tracking System—INDStation, p. 1-2.
Rebecca D. Kush, Edward Helton, Frank W. Rockhold, and C. David Hardison, Electronic Health Records, Medical Research, and the Tower of Babel, vol. 358:1738-1740, No. 16, Apr. 17, 2008, p. 1-4.
Monitoring and Management of Clinical Trials, NES—Clinical Trials—Monitoring and Management, p. 1-4.
News bulletin for small and medium-sized enterprises, Issue 3, February, p. 1-6.
John I. Gallin, Frederick P. Ognibene, Principles and practice of clinical research, Book Overview, Edition: Feb. 2007, p. 1-5.
Rebecca Daniels Kush, Standards to Link Clinical Research and the Electronic Health Record, Clinical Data Interchange Standards Consortium, CDISC Setting the Global Standard for Clinical Data, HP Health & Life Science Symposium, Jul. 17-20, 2006, p. 1-100.
M. Manuela Cunha, Antonio Tavares and Ricardo Simoes, Handbook of Research on Developments in e-Health and Telemedicine: Technological and Social Perspectives, Studies, Feasibility Studies, etc., Polytechnic Institute of Cávado and Ave, Portugal (http://ehealth_and_telemedicine.ipca.pt/), Copyright 1998-2008 © EHTO, Jul. 4, 2008, p. 1-8.
James Paul, Rachael Seib, Todd Prescott, The Internet and Clinical Trials: Background, Online Resources, Examples and Issues, Department of Anesthesia, Hamilton Health Sciences, Hamilton, ON, Canada, Department of Anesthesia, Faculty of Health Sciences, McMaster University, Hamilton, ON, Canada, p. 1-31.
The Rockefeller University Hospital—Clinical Research Support Office (CRSO), Center for Clinical and Translational Science, Copyright © 2004-2008 The Rockefeller University, p. 1-5.
Wiley InterScience: Journals: Statistics in Medicine, vol. 20 Issue 17-18, p. 1-2.
Glossary of Terms, Boehringer Ingelheim Global Clinical Trials website, p. 1-3.
Donald W. Rucker, Beyond the Electronic Medical Record, Global Digital Healthcare Integrated Delivery Systems Conference, Oct. 10-11, 2006, p. 1-4.
Responses to "The Future Vision of Electronic Health Records as eSource for Clinical Research" Draft Discussion Paper, version released for comment on Mar. 3, 2006 by the eClinical Forum and the PhRMA EDC/eSource Taskforce, p. 1-29.
Deborah Borfitz, Rave 5.6: A Single Database for EDC and CDM, Bio-ITWorld.com, Feb. 20, 2007, p. 1-7.
Guidance for Industry Providing Regulatory Submissions in Electronic Format—Human Pharmaceutical Product Applications and Related Submissions Using the eCTD Specifications, U.S. Department of Health and Human Services, Food and Drug Administration, Center for Drug Evaluation and Research (CDER), Center for Biologics Evaluation and Research (CBER), Jun. 2008, p. 1-20.
Deborah Borfitz, OpenClinica 2.5 Targets Industry-Sponsored Trials, Oct. 27, 2008, p. 1-2.

(56) References Cited

OTHER PUBLICATIONS

Press Release, GAO Announces Appointments to Health Information Technology Policy Committee, United States Government Accountability Office, Apr. 3, 2009, p. 1-3.
Adams CP, Brantner VV, Estimating the cost of new drug development: is it really 802 million dollars?, Bureau of Economics, Federal Trade Commission, in Washington, DC, USA. cadams@ftc.gov, Health Aff (Millwood), 25 (2):420-8, Mar.-Apr. 2006, p. 1.
HIPAA Privacy Agreement Form for Business Associate Contract, http://www.medlawplus.com/forminfo/hipaaprivacyagreement.htm, p. 1-2.
Clinical Data Interchange Standards Consortium, © 2008 Clinical Data Interchange Standards Consortium, Inc., p. 1.
Guidance for Industry 21 CFR Part 11; Electronic Records; Electronic Signatures Validation, Aug. 2001, p. 1-24.
FDA Select Study, p. 1.
Clinical Trial Operational Readiness, Webinar Series, Study Manager, Innovative CTMS & EDC Solutions, Jun. 11, 2009, p. 1-2.
Guidance for Industry Part 11, Electronic Records; Electronic Signatures—Scope and Application, U.S. Department of Health and Human Services, Food and Drug Administration, Center for Drug Evaluation and Research (CDER), Center for Biologics Evaluation and Research (CBER), Center for Devices and Radiological Health (CDRH), Center for Food Safety and Applied Nutrition (CFSAN), Center for Veterinary Medicine (CVM), Office of Regulatory Affairs (ORA), Aug. 2003, p. 1-12.
Glossary of Computerized System and Software Development Terminology, p. 1-61.
Guidance for Industry Incorporation of Physical-Chemical Identifiers into Solid Oral Dosage Form Drug Products for Anticounterfeiting, U.S. Department of Health and Human Services, Food and Drug Administration, Center for Drug Evaluation and Research (CDER), Jul. 2009, p. 1-11.
John D. Mestler, Suzanne Bishop, Richard Perkins, Catherine Celingant, EHR/CR User Requirements Document, EHR/CR Functional Profile Working Group, eClinical Forum, PhRMA EDC/eSource Task Force, Nov. 1, 2007, p. 1-29.
Patricia Holobaugh, Good Clinical Practices and FDA Inspections, p. 1-34.
Is your clinical trial CDISC compliant and ready for submission to the FDA?, Innoventz Corporation, p. 1-5.
Michael Owings, Alan Pollack, Comments Submission: Jan. 3, 2005, p. 1-2.
Beyond CRO, Innoventz Corporation, p. 1-4.
Electronic Records: Electronic Signature Certification, Inspections, Compliance, Enforcement, and Criminal Investigations, Department of Health and Human Services, Food and Drug Administration, FDA Home> Inspections, Compliance, Enforcement, and Criminal Investigations> Inspections> Field Management Directives, p. 1-4.
Maximizing the Effectiveness of Clinical Trials, Innoventz Corporation, p. 1-9.
Product Enhancements in Verity Federator v2.0, Nov. 3, 2004, p. 1-2.
The Quest to Enable the Electronic Clinical Trial: Finding Clarity in a Confusing World, Drug Information Association Conference, Dec. 6-7, 2006, p. 1-8.
Adobe Electronic Forms for Clinical Development, © 2005 Adobe Systems Incorporated, p. 1-2.
Rob Tidwell, Guidance for Industry Computerized Systems Used in Clinical Trials, p. 1-26.
Ronald Marks, The Status of e-Clinical Trials, Reference Section, Business Briefing: Pharma Outsourcing, p. 1-3.
Joanne L. Rhoads, E-Source: FDA Regulatory Background and Concerns for Implementation, Jan. 25, 2006, p. 1-25.
Praxis and the Concept Processor: "Charting Bass Ackwards", © 2006 Infor-Med Medical Information Systems Inc., Aug. 31, 2006, p. 1-9.
Evaluation & Management Services Guide, Jul. 2006, p. 1-32.
Randy Levin, Impact of Regulations on Data Management Practice, DIA 12th Annual European Clinical Data Management Conference, Working within Changing Boundaries, Nov. 5, 2002, p. 1-37.
EDC Adoption in Clinical Trials: A 2008 Analysis, Feb. 2008, p. 1.
Guidance for Industry, Electronic Source Documentation in Clinical Investigations, Draft Guidance, U.S. Department of Health and Human Services Food and Drug Administration Office of the Commissioner, Dec. 2010.

\* cited by examiner

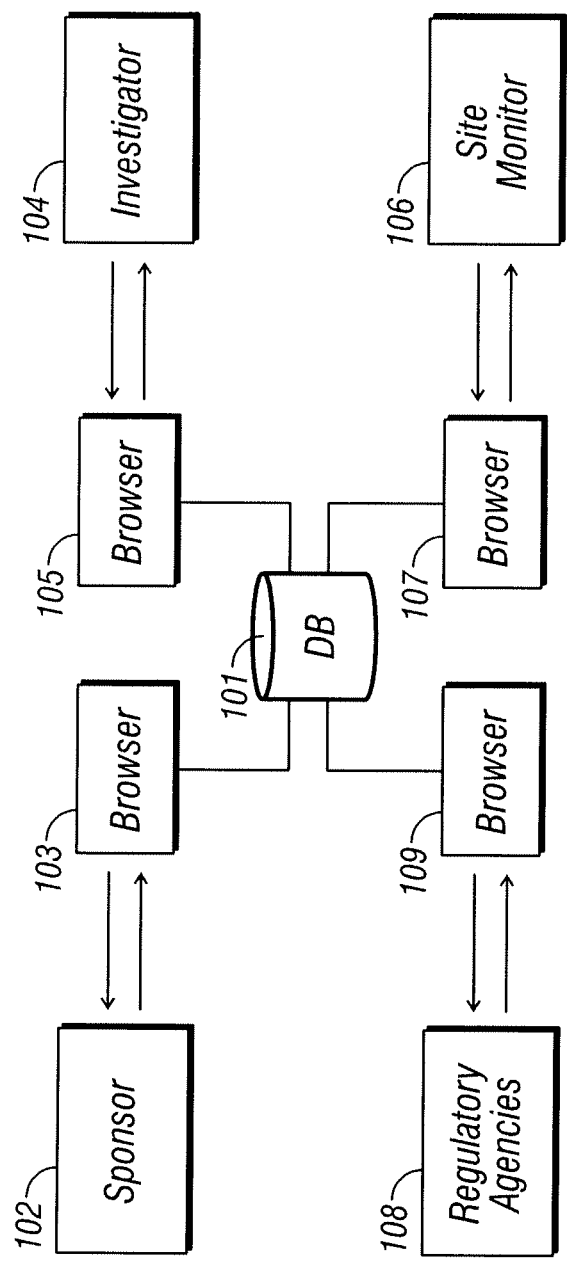

SYSTEM FOR ELECTRONICALLY RECORDING AND SHARING MEDICAL INFORMATION

STATEMENT OF RELATED CASES

The instant application is a continuation-in-part of prior U.S. non-provisional application Ser. No. 12/339,748 filed Dec. 19, 2008, now abandoned, which claims the benefit of prior U.S. provisional application No. 61/008,326, filed Dec. 19, 2007.

FIELD OF THE INVENTION

The present invention relates generally to the field of medical data, and in a particular though non-limiting embodiment to a system for centralizing electronic clinical trial data in such a manner that original patient data and original clinical trial data are accurately recorded, stored and protected in a central database that contains both original patient data and original clinical trial data in a clinical trial electronic source document.

BACKGROUND

The United States Food and Drug Administration (FDA) typically evaluates a drug or a device prior to approving or rejecting it for human consumption or use. The FDA approval process involves determining the safety and effectiveness of the drug or the device in question by reviewing data from clinical trials, in which the drug or device is administered under controlled conditions. Clinical trials often begin with a single study that includes a small number of subjects located at one testing facility, and then gradually progress to include many studies of increasingly larger numbers of subjects located at numerous, geographically dispersed, testing facilities. The entity seeking drug or device approval compiles the data from these trials and then submits the data via direct delivery, mail, fax, email, and data uploads, PDF, etc., to the FDA for review.

The FDA only considers data that are identical in nature to the original data, which are recorded in what is known as source documents. All other transcriptions, iterations, compilations, analyses and interpretations of the data are derived from and are dependent upon the data as they were originally recorded in the source documents, which traditionally have been hand written.

Those of skill in the pertinent arts will readily appreciate that the FDA's acceptance of data from clinical trials for decision-making purposes depends primarily upon the authenticity, quality, and integrity of the original data which the FDA determines during on-site inspections and audits, the results of which it compares with the data that the sponsor has submitted to the FDA in support of its new drug application.

Recent federal regulations and FDA guidance documents have provided for the existence of electronic source documents and have defined significant terminology and requirements for electronic source documents. For example, a recent FDA article entitled *Guidance for Industry: Computerized Systems Used in Clinical Investigations*, U.S. Department of Health and Human Services, Food and Drug Administration, Office of the Commissioner (May 2007), " . . . provides to sponsors, contract research organizations (CROs), data management centers, clinical investigators, and institutional review boards (IRBs), recommendations regarding the use of computerized systems in clinical investigations. The computerized system applies to records in electronic form that are used to create, modify, maintain, archive, retrieve, or transmit clinical data required to be maintained, or submitted to the FDA." The source data are necessary for the reconstruction and evaluation of the study to determine the safety of, for example, food and color additives, or the safety and effectiveness of new human and animal drugs, and medical devices; consequently, this guidance is intended to assist in ensuring confidence in the reliability, quality, and integrity of electronic source data and source documentation (i.e., electronic records). Id. at p. 1, q.v.

This same guidance document provides an abbreviated list of definitions of terms commonly used in FDA guidance documents in this context:

An audit trail is a process that captures details such as additions, deletions, or alterations of information in an electronic record without altering the original record. An audit trail facilitates the reconstruction of the course of such details relating to the electronic record.

A certified copy is a copy of original information that has been verified, as indicated by a dated signature, as an exact copy having all of the same attributes and information as the original.

A computerized system includes computer hardware, software, and associated documents (e.g., a user manual) that create, modify, maintain, archive, retrieve, or transmit in digital form information related to the conduct of a clinical trial.

Direct entry is a method of recording data wherein an electronic record is the original means of capturing the data. Examples include the keystroke entry of original observations into a system by an individual, an automatic recording generated by a scale that measures a subject's body weight, etc.

An electronic record is any combination of text, graphics, data, audio, video, or other information representation in digital form that is created, modified, maintained, archived, retrieved, or distributed by a computer system.

Original data are those values that represent a first recording of study data. The FDA currently allows original documents and the original data recorded on those documents to be replaced by copies, provided the copies are identical and have been verified as such.

Original documents and records include, but are not limited to, hospital records, clinical and office charts, laboratory notes, memoranda, subjects' diaries or evaluation checklists, pharmacy dispensing records, recorded data from automated instruments, copies or transcriptions certified after verification as being accurate and complete, microfiches, photographic negatives, microfilm or magnetic media, x-rays, subject files, and records kept at the pharmacy, at the laboratories, and at medico-technical departments involved in a clinical trial.

Transmit is a method of transferring data within or among clinical study sites, contract research organizations, data management centers, sponsors, or to the FDA.

Id. at p. 8.

In order to prevent fraud when investigators and sponsors have access to the same system, a clinical investigator must retain records required to be maintained for a particular period of time as specified in the relevant regulation. This requirement applies to the retention of the original source document, or a copy of the source document. When source data are transmitted from one system to another (e.g., from a personal data assistant to a sponsor's server), or entered directly into a remote computerized system (e.g., data are entered into a remote server via a computer terminal that is located at the clinical site), or an electrocardiogram at the clinical site is transmitted to the sponsor's computerized system, a copy of the data should be maintained at another location, typically at the clinical site but possibly at some other designated site. Copies should be made contemporaneously with data entry and should be preserved in an appropriate format, such as XML, PDF or paper formats.

The FDA considers 'original data' to be "those values that represent the first recording of study data." Id. at p. 8. "When original observations are entered directly into a computerized system, the electronic record is called the source document." Id. at p. 4.

Ideally, a system would exist that would admit to direct entry of all the original data of a clinical trial into a single computerized system, the electronic record of which would reside in one location, in one database. The electronic record would include an audit trail that captures any and all details such as additions, deletions, or alterations of information in the electronic record without obliterating the original record. This electronic record would be the clinical trial source document, and it would be available for entry or review in real-time from even remote locations. For example, the electronic source document, in such an ideal system, would enable the sharing of original data, in their original forms, within or among clinical study sites, contract research organizations, data management centers, the sponsoring organization, institutional review boards, or the FDA. Data transcriptions, case report forms, the transfer of data between and among servers would no longer be necessary. Further, the need for copies made contemporaneously with data entry and preserved in a format such as XML, PDF or paper may also become obsolete.

This ideal approach is not, however, currently utilized in any known system. To the contrary, source documents in clinical trials tend to be heterogeneous documents maintained in decentralized locations and primarily recorded on paper. Even in medical offices that use electronic medical records systems (EMR's), these EMR's are typically not suitable for use as the source documents for clinical trials: they lack the structure and means to accommodate both patient and clinical trials data together in a single system, do not fulfill all the requirements associated with sponsor designs, regulatory guidelines and requirements, etc., and are usually compilations of documents, transcriptions, dictation uploads, and other entries that are not original in nature.

The documents for a clinical trial are created by, and reside at the disparate and unconnected locations of, the assortment of principals involved in the various parts of the clinical trial. The principals who create and/or review clinical trial data include a sponsoring organization, such as a pharmaceutical company or other party interested in the approval of a medicine or device ("sponsor"), whose application to the FDA for the approval of its drug or device includes the submission of protocols and study plans (e.g., requirements, procedures, schedules) for the clinical trials; a plurality of clinical investigators ("investigators"), who recruit subject patients that meet the clinical trials requirements, gather and record their medical history information (e.g., illnesses, conditions, medications, operations, medication allergies, etc.) before, during, and at the conclusion of the trial, interpret the clinical trial study plan and then perform the study visits and procedures on the subject patients, including the administration of the test drug or device and documenting the subject patients' responses to it; an ethical or institutional review board ("IRB"), that monitors the activities of the sponsor and the investigator sites to protect subject rights and safety; and the miscellaneous other providers of services and supplies ("vendors"), such as the manufacturer and shipper of the test agent and the clinical and analytical laboratories that analyze subject samples.

Currently, the source documents themselves are not submitted to the sponsor by the investigators, the IRB, or the vendors. Instead, each entity extracts whatever original data elements are required by the protocol and then submits transcriptions of the data elements by using either paper or electronic proxies for the original data. For example, the sponsor usually requires that the investigators transcribe data from the source documents to paper or electronic forms, called case report forms. The data contained in these case report forms, in turn, comprise a centralized repository for the proxy data. The sponsor analyzes the proxy data and then submits PDF versions of the case report forms, copies of the centralized proxy data repository, and its analyses of the data to the FDA. Since the case report forms, the central proxy data repository, and the PDF forms are not the original data, however, the Sponsor and the FDA must verify the proxy data against the original data, and they also must determine whether the original data are true, accurate, authentic, and in compliance with the requirements of the protocol, by viewing the actual source documents at the various locations where the source documents physically reside.

These sponsor and FDA on-site reviews of the source documents often reveal errors and discrepancies among the clinical trial protocol and study plan requirements; the investigators' interpretations of the study protocol and its study plan and procedures; the procedures actually performed; the types and formats of data gathered during the trial; the source document data; the case report form (proxy) data; the sponsor's intermediate and final databases; and the data and documents reviewed by the FDA. These findings often lead to the invalidation of some or all of the clinical trial data.

Currently, the sponsor, depending upon the size and duration of a particular clinical trial, typically is able to send site monitors to perform its reviews of the source documents at the investigator sites only at the conclusion of a trial and periodically during the trial, usually no more frequently than every six weeks. This means that significant findings of protocol non-compliance, subject safety issues, errors and omissions in source documentation, and discrepancies between the original data in the source documents and the proxy data in the paper or electronic case report forms may go unidentified for weeks or months; or that identification of data patterns that might suggest a need to revise the protocol for safety or scientific reasons are too late to be actionable.

Currently, the FDA typically reviews source documents only after the clinical trials are completed and after the sponsor has submitted the resulting data to the FDA. Further, the FDA does not have the resources to visit every geographically dispersed testing facility. With the increasing number of domestic and global facilities and international studies taking place, the FDA usually only selects a limited number of facilities to inspect following completion of clinical trials, so that most clinical trial source data has not yet been verified by the FDA before a drug or device for human consumption or use is approved.

Thus, current clinical data systems waste time and resources at each step in the drug development, testing and approval process; place study data integrity and study patient subjects at risk; potentially endanger wider patient populations who become exposed to the drug or device after it has been approved following inadequate regulatory review of clinical trial source documents; and preclude timely and strategic decision-making by sponsors, IRBs, and the FDA in the drug development, testing, and approval processes.

Recent attempts to centralize the proxy data by electronic means include filters and prompts at both the decentralized site computers and at an intermediary information center database in order to facilitate "cleaning" the data (reconciliation of discrepancies between original data and proxy data), before the proxy data are uploaded to a final database for final analysis and then submission to the FDA. While these features are intended to improve the quality of proxy data, they would be out of place in a system that centralizes original data, since the imposition of intermediary feedback signaling and filtering systems would introduce the possibility of biasing the data and invalidating the process of collecting true and original observations in the form of original data as recorded in an electronic source document.

There is therefore, a long-felt but unmet need for a secure and reliable electronic source document generation and storage process in which medical history and clinical trial data can be recorded and verified in a globally consistent manner. Likewise, as electronic document systems expand more generally (e.g., government mandated electronic medical records, electronic prescriptions, insurance processing, etc.), there will be an ongoing need for secure and reliable electronic source documents in which data can be recorded, verified, and shared among authorized entities (e.g., the patient, the patient's health care providers, regulators, etc.) in a manner consistent with the requirements of such programs. The availability of such a centralized electronic source document system will also help meet the ongoing needs to facilitate the recruitment of subjects for clinical trials; patients' locating studies in which they might want to participate; the evaluation of the relative benefits of different treatment regimens in large populations for planning improved treatment and drug development programs for better health outcomes; and capturing medical conditions for the FDA Adverse Event Reporting System (AERS) by tracking subjects' medical histories not only during but also after they complete trials.

SUMMARY OF THE INVENTION

A system for electronically recording and sharing medical data is provided, the system comprising an electronic source document, wherein the electronic source document comprises a database. In one particular embodiment, the medical data comprises clinical study data. In some embodiments, the system further comprises means for defining parameters of medical data and storing the medical data parameters within the electronic source document, as well as means for entering medical data into the electronic source document and storing the medical data therein. In a further embodiment, the system comprises means for one or more users of the system to view stored medical data. In a still further embodiment, the system further comprises means for one or more users to amend or modify medical data stored in the electronic source document, and in yet another embodiment the system comprises means for creating and maintaining an audit trail when one or more of the users amends or modifies medical data stored in the electronic source document. In other embodiments, the system further comprises an application specific navigation tool; in some embodiments, the application specific tool comprises a graphical user interface. In still other embodiments, the means for entering medical data further comprises a browser, and in still other embodiments the browser is disposed in communication with said electronic source document by means of one or more of an Internet connection, an Ethernet connection, a Bluetooth connection, an 802.11g connection, a wireless cellular connection, a hard wired computer terminal connection, a voice recognition or touch activated screen, a personal digital assistant, and a portable data management device. Appropriate methods of using the system are also provided.

In another embodiment, a system for electronically recording and sharing medical data is provided, the system comprising an electronic source document, wherein the electronic source document comprises a database. In some embodiments, the system comprises means for defining parameters of patient data and storing the patient data parameters within the electronic source document, as well as means for entering patient data into the electronic source document and storing the patient data therein. In a further embodiment, the system comprises means for one or more users of the system to view stored patient data. In a still further embodiment, the system further comprises means for one or more users to amend or modify patient data stored in the electronic source document, and in yet another embodiment the system comprises means for creating and maintaining an audit trail when one or more of the users amends or modifies patient data stored in the electronic source document. In other embodiments, the system further comprises an application specific navigation tool; in some embodiments, the application specific tool comprises a graphical user interface. In still other embodiments, the means for entering patient data further comprises a browser, and in still other embodiments the browser is disposed in communication with said electronic source document by means of one or more of an Internet connection, an Ethernet connection, a Bluetooth connection, an 802.11g connection, a wireless cellular connection, a hard wired computer terminal connection, a voice recognition or touch activated screen, a personal digital assistant, and a portable data management device. Appropriate methods of using the system are also provided.

BRIEF DESCRIPTION OF THE DRAWINGS

The single drawing in the case illustrates a representative embodiment of the invention in which sponsors, investigators, remote site monitors and third parties utilize a common electronic source document such as a database to record, store and share original medical data obtained before, during and after a patient's participation in a medical clinical study.

DETAILED DESCRIPTION

A major obstacle preventing centralization of source documents for clinical trials is the same obstacle that impedes the universal adoption of electronic source documents generally, viz., the difficulty incorporating (e.g., capturing, entering, recording, etc.) the non-linear, multidimensional workflow of health care providers within a single digital system that presents and organizes desired information linearly. In fact, the methods of navigation, entry, storage, and retrieval of data in today's typical electronic medical records (EMR) system are so unpopular that their adoption has required a federal mandate, and the enigmatic complexity of the information flows in the clinical environment has eluded their replacement by a better system that sponsors and health care workers can use for clinical trials.

The shortcomings of EMR's come in part from their evolution as a narrative style of paper medical charting, so they use a document- and template-driven approach that has resulted in clinical information that are typically not sufficiently digitized, and navigation that is not sufficiently flexible, to accommodate an object-oriented data management structure and format. As a result, they force the user to perform tasks in specific sequences, reaching forms and reports down restricted, linear, cascading pathways that lack the flexibility needed for the more varied and variable ways that information flows as health care workers interact with patients in actual clinical practice. Furthermore, their reliance on document-driven formats, incomplete digitization of data parameters and absence of audit trails preclude their use in clinical trials.

Another obstacle to centralization of source documents for clinical trials has been the scientific and regulatory imperatives for the control of data access in ways that preserve investigator independence, patient privacy, and clinical data security within one system. Lacking any other commonly accepted solution, the industry has defaulted to the continued use of heterogeneous source documents, case report forms, and proxy data, with all their attendant deficiencies.

Accordingly, means are provided herein for delivering highly structured data while providing continuous flexibility for data entry that can originate from a variety of input sites within a single, commonly shared electronic source document. In this manner, investigators' recording of patient medical histories and clinical data—which are often collected and entered in non-sequential, non-linear work patterns—all occur within a single electronic source document system that delivers related original data to principals in a manner that will not compromise the integrity of the study or the rights, safety and privacy of patients.

In an example embodiment, one or more principals define the types of data and the schedule and manner of collecting them of a desired clinical study and the type and structure of data required for collection and storage in an electronic source document. Principals can include a sponsoring organization (sponsor), which is often a pharmaceutical company, a contract research organization (CRO) hired by the sponsor, an Institutional Review Board (IRB), or any other such entity involved in the conduct of trials for the approval of a new drug or device. In further embodiments, a medically licensed clinical investigator (investigator) recruits test subjects, conducts clinical studies, evaluates responses, etc., and is responsible for entering medical history and clinical trial data into the electronic source documents. In some embodiments, the 'investigator' also comprises a physician and/or other health care worker not directly involved with the clinical study, but otherwise involved in the medical care of a patient and authorized to enter and review certain patient data. In other embodiments, the principal creates a graphical user interface in order to standardize the subsequent clinical data entry process. In still other embodiments, access is given to sponsors to view or otherwise monitor, e.g. by means of a browser or the like, subject data collected and input by investigators. In still others, the clinical investigator also utilizes one or more graphical user interfaces that facilitate the entry of data in non-sequential, non-linear ways, into the electronic source document. The various graphical user interfaces may in some instances be the same for both the sponsor and the investigator, or they may vary depending on the access and permissions granted to the user, based upon FDA Good Clinical Practices Guidelines, The Health Insurance Portability and Accountability Act (HIPAA), and federal regulations governing clinical trials conventions and the privacy of patient information.

Various embodiments permit principals to view clinical study data and/or patient data and query other principals about the content or reliability of the data, but separate authorizations in order to preserve the scientific integrity of the trial and the rights of the participants in the trial. Such embodiments would provide a means to control access and permissions to the system and its component parts, including the forms and reports, controls on the forms and reports, and the database tables that comprise the electronic source document. Additional embodiments safeguard the scientific integrity of the trial and the privacy rights of the patient subjects in the trial by allowing the sponsor and other entities to view the clinical trial data, but restricting them from entering or altering patient and clinical trial data and from viewing patient protected health information (PHI). In one embodiment, only the sponsor is permitted to create and edit electronic source document templates while only the investigator is permitted to interact with patients and enter subject data generated during the clinical study. This structure safeguards protocol compliance by helping to assure that the investigator collects the types of data required by the sponsor, the FDA, etc., for the study-specific source document and by preserving the independence of the investigator's control of patient data. In another embodiment, for patient data, a patient's protected health information (PHI) can only be entered, modified, and viewed by the patient's physicians/investigator and their staffs; and other actions for patient data or the patient's study data can be further restricted, so that, for example, assigning clinical significance or causation to a patient's adverse event or condition can only be entered and modified by the patient's physician/investigator and no one else. At the same time, all patient data (other than PHI, which is restricted to the patient's physicians/investigator and their staffs) and physician/investigator actions can be viewed by any authorized principal, including the patient's physicians/investigator, investigator staff, the sponsor, the IRB, and the FDA. By contrast, for clinical trial-specific data, in one embodiment, only the sponsor can define the study-specific parameters, like the study medication dosing and procedure schedules and the safety and efficacy evaluation data parameters; only authorized principals—other than the sponsor—can enter and modify the data required by those specifications. At the same time, all authorized principals can view the clinical trial-specific parameters and the data as their access permissions allow.

Such embodiments provide a means to control access and permissions to the system and its component parts, including the forms and reports, controls on the forms and reports, and the database tables that comprises the electronic source document. For example, for patient data, a patient's protected health information (PHI) can only be entered, modified, and viewed by the patient's physicians/investigator and their staffs; and other actions for patient data or the patient's study data can be further restricted, so that, for example, assigning clinical significance or causation to a patient's adverse event or condition can only be entered and modified by the patient's physician/investigator and no one else. At the same time, all patient data (other than PHI, which is restricted to the patient's physicians/investigator and their staffs) and physician/investigator actions can be viewed by any authorized principal, including the patient's physicians/investigator, investigator staff, the sponsor, the IRB, and the FDA. By contrast, in another example, for clinical trial-specific data, in one embodiment, only the sponsor can define the study-specific parameters, like the study medication dosing and procedure schedules and the safety and efficacy evaluation data parameters; only authorized principals—other than the sponsor—can enter and modify the data required by those specifications. At the same time, all authorized principals can view the clinical trial-specific parameters and the data as their access permissions allow.

In other embodiments, principals interact with one another in real-time as they view the identical original, data, at the same time, even as soon as immediately after the data are entered, and even from different locations. For example, by obviating the need for data transcription agents, site monitoring, data validation, intermediate evaluations, etc., prior to loading the contents of an electronic source document into a final database destination for review and analysis, in such an embodiment, the investigator and the sponsor are able to view the same original data concurrently, proximate enough in time to the event that generated the data, so that a regulatory compliance, protocol compliance, or safety issue can be identified and corrected in a timely manner and not languish, as may occur today in current systems. This improved, real-time investigator-sponsor communication allows immediate identification and rapid resolution of patient safety issues, protocol compliance issues, and data signals that may indicate the need to amend or otherwise modify the protocol, without data corruption or delay. Such embodiments can result in improved patient safety, regulatory compliance, shorter drug development times, and more cost-effective drug discovery and development programs.

By enabling remote access to electronic source data, typical example embodiments will improve upon the FDA's current practice of only selecting a limited number of inspection facilities following completion of clinical trials. Remote access will allow the FDA to inspect and attain a more comprehensive data evaluation from anywhere and at any time during or after a clinical trial, even as number of worldwide testing facilities continues to increase. Among other benefits, for example, safety or fraud issues (e.g., Vioxx safety data) that otherwise might be buried in the source data are easily identified using the presently disclosed data management system.

Another embodiment includes an auto-query process by which data entered into the electronic source document are compared against predetermined data parameters, any violation of which will result in a query to the investigator. The auto query, the investigator's original response or action, and any subsequent modifications of the original data in response to the query, are tracked in an audit trail. This process differs from the current practice of using prompts or filters appropriate for improving the quality of proxy data, but that would not be used in the current invention, which provides for the recording, storage, sharing and tracking of original data. For example, in one embodiment of the present invention, the entry for a blood pressure result of '200' (the required range being 120-140) would be recorded and stored in the database without intervention, and any query would occur only afterwards; whereas, current proxy data systems would block the entry with filters and prompts to prevent a transcription error.

Still other example embodiments permit investigators, sponsors, IRB's, or the FDA to enhance the FDA's post-approval adverse events monitoring program (AERS), which the FDA has warned lacks sufficient voluntary subscription to be comprehensive, and for which no other tool is currently available for monitoring patient subjects or post-approval adverse drug reactions. This embodiment would permit the continued surveillance of subject patients' ongoing medical histories (events, conditions, adverse events, medications, operations, etc.), directly, even after they have completed the clinical trials.

The specific description that follows includes exemplary systems and methods that embody various data handling techniques related to the presently inventive subject matter. However, it will be readily understood by those of ordinary skill in the art that the embodiments described herein may be practiced without one or more of the specific details employed in the description. In other instances, known equipment, protocols, structures and techniques have not been shown in detail in order to avoid obfuscation in the description.

SPECIFIC EXAMPLE EMBODIMENT

In the present invention, the study's original data are the exact same data collected by investigators, queried by sponsor site monitors, analyzed by the sponsor, and reviewed by the FDA, etc., because all data in the study are entered directly into a single unified electronic source document such as a database. Data collected and stored in this fashion can then be queried, audited, compiled, downloaded, etc., without compromising the data and therefore the integrity of the study. Similarly, edits and modifications to the data can be either prohibited or allowed, or strictly controlled and recorded subject to various predetermined authorizations and permissions designed and implemented in such a manner that a permanent, reliable audit trail is created that reflects all such activity.

Unlike the prior art data management systems, there is no transcription of hand-written notes, no data filtering, and no prompting or cleaning in intermediate databases. Entry, storage and delivery of the data in their original form, without intervening translational steps, assures the data are both accurate and valid. Centralization of the original data in a single electronic source document enables remote access to all original data present in the study (subject to various authorizations, hierarchies, etc.), and obviates the need for on-site verifications by sponsors and regulatory agencies.

Since the original data are the exact same data collected and entered into the electronic source document, all pertinent data to which an authorized party is allowed access are available immediately, in real-time, as they are entered and without delay. Real-time access to original data means that sponsors can ensure timely conformity and consistency with predefined protocols, study plans and regulatory document requirements. Such availability also enables timely oversight of subject safety by sponsors, IRBs and regulatory agencies; timely trial management and decision making, as well as remote monitoring of the trial; and transparent and accountable oversight by the IRBs and regulatory agencies such as the FDA.

The attached FIGURE is a flow diagram detailing illustrative aspects of the invention's capacity for creating, modifying, viewing and sharing the data contents of an electronic source document. The actual structure of the system is in fact open-ended, and can include any number of users acting in additional or different roles, each of whom may in a given study be tasked with greater or fewer duties, so long as it is understood that all data accumulated and entered by any user in the system are originally recorded into a single electronic source document. In a presently contemplated commercial embodiment, the electronic source document is created within a database, and data entry is facilitated by a series of remote browsers using graphical user interfaces, though other configurations can be used to achieve the functionality required herein.

The attached FIGURE illustrates how the entire medical data management system is centered about a single, commonly shared electronic source document 101. In a presently contemplated embodiment, the electronic source document 101 consists of a database, wherein certain contents are made available to certain users, while other data are not shared between or amongst users. To set up the system for a clinical trial, the first data entered into the system will generally be the sponsor data 102, which is entered directly into the electronic source document 101 by means of a browser or the like 103. The types of data entered by each sponsor can vary (e.g., in various embodiments sponsors may define the types of information and the manners in which certain records are to be entered and stored, whereas in others, protocols for the study are tied to particular agency-compliant forms, etc.), but it is highly desirable that the sponsor data or data requirements not be recorded in any other medium or any other location other than within the electronic source document 101. It is apparent, for example, that if a sponsor 102 defines data fields relating to the study on its own system or in another locally stored manner (e.g., as would be the case if browser 103 were instead a local terminal in which the protocols are first developed and stored and then uploaded to the database 101), there will necessarily be a delay in the process, as investigators 104, site monitors 106 and regulatory agencies 108 cannot view, download, comment upon or otherwise interact with the data until it is uploaded to the database 101.

On the other hand, when a sponsor defines the data fields required for a clinical study directly within an electronic source document such as a common database, there is no possibility of delayed access, data corruption, improper execution due to timing issues or shared physical resources during upload, etc., and there is also less likelihood that the investigators would violate the study plan, since the data requirements reside in the source document unambiguously. In typical embodiments, the sponsor-created portion of the electronic source document consists of general or specific trial parameters, lists of data desired for collation, schedules of activities and data requirements, agency-compliant forms, etc., each presented in an appropriate graphical user interface that allows a user to either enter data directly, or instead be directed to an appropriate data entry point. In various other embodiments, the interface is web-based or integrated using another application, etc., so long as the interface contains an electronic means for communicating directly with the centralized database 101.

In some embodiments, clinical studies are defined by a plurality of sponsoring organizations or companies whose individual data are collectively required in the approval of a new drug, medicine or device. In one example embodiment, a pharmaceutical company applying for approval from the FDA for a new drug or medicine initiates a clinical study containing data requests defined by an IRB, providers of related services or supplies, such as providing the study medication, etc. The defined data elements and required forms are then entered directly into a common electronic source document 101, where they can be viewed by regulatory agencies 108 and others with an interest in the development of the study.

Once defined, similar electronic means are provided to permit direct electronic entry of patient and study data by a plurality of investigators 104 and their staffs. According to certain example embodiments, relevant patient data include information describing the condition and characteristics of a patient, for example, the name, age, height, weight, blood pressure, apparent physical condition, etc., as would typically be recorded for identification and historical purposes. More detailed patient data might include, for example, descriptions of drug regimens taken by the patient, injury and disease history, both pre-existing and as occur during the trial, and other data pertinent to the specific objectives and requirements of the trial, etc.

Typically, data are entered directly into the electronic source document 101 using a graphical interface operated by means of a browser or the like 105. It is essential for the scientific integrity of the trial that the original data be entered into the electronic source document 101 without any intervening written reduction, and interface checklists and other predetermined characteristic features can be provided in order to reduce inadvertent errors in that respect. In one embodiment, the database is encoded with commands to prevent submission of data entered into a graphical user interface if the data are not understood or contain syntax errors. In other embodiments, the database is encoded with commands to alert or query a clinician if certain predetermined data are omitted or entered incorrectly.

In some embodiments, the original data form created in the electronic source document 101 cannot thereafter be altered or amended except by means of a previously determined protocol that has been designed to ensure the integrity of the trial. For example, text comments or queries or text messages exchanged among the principals are memorialized in unaltered and unalterable states in the database for retrieval and viewing in conjunction with their contextual references. In an exemplary case, when a site monitor is alerted that a particular investigator's data submission history is deficient, the monitor enters an inquiry that the system stores and then sends to the clinician to re-evaluate certain portions of certain forms, etc., in order to demonstrate the problem, or to request that the investigator amend the record if the investigator thinks it should be amended. Since both the investigator 104 and the monitor 106 are linked by means of the electronic source document—and are in fact looking at the same data, even possibly at the same time—it follows that an audit trail of all such communications and proposed or actual amendments is easily compiled within the data base 101.

It is contemplated that the system will comprise multiple embodiments of the audit trail in the event that various formats of the audit trail are required by different categories of data, changed data, proposed data changes, and/or different sponsors' or regulatory agencies' requirements. For example, in the typical embodiment, the audit trail of a record's data changes includes at least the following: the old data, the new data, the user who makes the change, the reason for the change, the date of the change, and the time of the change; e.g., when Investigator 104 changes the name, dose, and indication of a patient's concomitant medication based upon new information. In another instance, where the audit trail comprises occurrences or events in the trial or communications among principals, the audit trail tracks additional or different data fields; e.g., the system's automatic detection of a protocol violation, with its data elements, contextual references, all users notified, with date and time stamps, and their actions, with date and time stamps; the user who originates a query and the relevant data fields queried, with date and time stamps, subsequent users, actions, and other relevant data in the trajectory of events, etc.

In further embodiments, communications and data shared between the investigator 104 and the sponsor's or the CRO's site monitor 106 are stored in the electronic source document without prior reduction, interference, filtering, validation, etc. Acceptance and retention of communications and original data in this manner safeguards the integrity of a test patient's data, or other study data, and assures that complete data transparency is maintained at all times. In some cases, it may be desirable to alert the sponsor, or the investigator, or both, about a datum value that falls outside specific parameters, to facilitate corrective action. In one embodiment, means are provided for the sponsor to define those data parameters within the database; the investigator to enter the data into the data fields; the data to be stored in the database; the database to evaluate the value of the data; and the system to alert the designated parties of any value that exceeds the parameters.

The specific electronic protocol used to carry out such communications is essentially irrelevant, so long as the required functionality of the system and the audit trail are maintained. For example, data can be transmitted to the database remotely via a wired or wireless global communications link, such as an Internet connection, an Ethernet connection, a Bluetooth connection, SONET, an 802.11g connection, a wireless cellular connection, a hard wired computer terminal connection, a voice recognition or touch activated screen, a PDA, or a portable data management device, etc.

Because the scope of a regulatory agency's involvement with a study is not necessarily co-terminus with the focus of the sponsor's study (for example, the FDA may wish to compile particular patient data for collation with health data from unrelated studies), it is important that the regulatory agencies 108 have access to clinical data in a timely, organized fashion. Systems employing translation, encryption or summation of data are inherently in tension with the government's desire to obtain original, unadulterated data quickly, so it is contemplated within the scope of the invention that regulatory agencies and other authorized third parties 108 have access 109 to the commonly shared electronic source document 101.

In a very specific example of the invention, a sponsor 102 uses a browser 103 to enter study and form requirements directly into a database 101, which serves as the centralized electronic source document. The sponsor information is then immediately available to all authorized principals, including investigators, monitors, vendors, and regulatory agencies alike, according to the specific and restricted permissions granted to each user. In this manner, the system ensures comprehensive and unambiguous specificity of each and every protocol requirement by detailing each and every study procedure for its fulfillment at the clinical investigator site during the investigator-study subject interface. Clinical investigators 104 then use a similar electronic means 105 to enter original patient data and study data into the database 101. In one embodiment, a clinician with access to and use of the system prior to initiation of the trial has already entered original patient data into the database. In such a case, the clinician can then enroll the patient into the study seamlessly, and the patient's study-specific data would be shared with authorized principals of the study.

In the event an investigator requires assistance, his needs become known and he can communicate directly with the appropriate party. For example, if the investigator cannot open a form provided by the sponsor, the investigator can communicate directly with the sponsor and request a corrected form. If on the other hand the investigator seeks guidance regarding which information to enter into a working form, he may alert the sponsor monitor so that the process can be observed and acted upon. For example, an investigator may be uncertain whether a particular patient's medical history or other characteristics meet the trial's entrance requirements. The investigator enables the sponsor to review the patient record in a manner that protects the patient's HIPAA requirements, to determine that patient's suitability for enrollment. Again, all such evaluations and communications would be preserved in the audit trail for regulatory review and scrutiny. Similarly, the sponsor/site monitor can communicate with the sponsor in the event the monitor requires clarification from the sponsor, is concerned with the integrity of the investigator's data acquisition process, or with the FDA if the sponsor becomes concerned that the trial protocol endangers a subject patient or is required to report a serious adverse event to the MRB and to the FDA. Finally, the FDA can view the data of all parties to facilitate a faster and more accurate review process, and can even compile and analyze data unrelated to the goals of the study if desired. The system's open architecture ensures transparency and validity of the study, and the possibility of expanding the system to accommodate additional studies with much larger populations is achieved. In yet another example embodiment, in the event the investigator needs to share patient data with the subject's physician, at the same or at a remote location, the system allows the patient's record to be shared, real-time, between the investigator and the physician, or among physicians, by predetermined protocols that protect the patient's rights and privacy and data integrity by including means for HIPAA authorization and user permissions that control access to the entry and review of patient and study data.

Those of ordinary skill in the pertinent arts will appreciate that additional electronic interfaces and peripheral devices can be added to this system to deliver printed or electronic reports of the data from the electronic source document database under an authorization protocol. For example, while the invention obviates the need for the case report form, one embodiment may generate an analogous output report, with the data fields required. However, in contrast with the current case report form, which is a transcription of source data and hence contains proxy data, the inventive report contains original data that comes directly from the electronic source document.

Data modules, management tools, and graphical interfaces useful with the architecture described herein can also be combined with the centralized electronic source document to ensure reliability, accuracy and integrity of patient data and a medical study. As evidenced by the inventor's disclosure in the underlying provisional application from which the instant application is derived, a number of such modules are in fact already contemplated for commercial use. Detailed graphical user interfaces, methods and means of effective database management, and methods and means of interaction between modules and management tools are also contemplated. These are fashioned and constructed to accommodate the non-linear work flows of health care workers as they interact with patients.

The foregoing specification is provided for illustrative purposes only, and is not intended to describe all possible aspects of the present invention. Moreover, while the invention has been shown and described in detail with respect to several exemplary embodiments, those of ordinary skill in the pertinent arts will appreciate that minor changes to the description, and various other modifications, omissions and additions may also be made without departing from either the spirit or scope thereof.

The invention claimed is:

1. A system for recording and sharing medical record data or data relating to a medical clinical trial and patient data associated therewith in a manner that creates and preserves an electronic record of stored original data so that a verifiable electronic source document is created and preserved, said system comprising:

a first electronic processing device disposed in communication with a software package that is capable of variably and selectively defining a plurality of access and permissions managers selected from medical care and clinical trials principals in an access and permissions manager selection set comprising a physician, a licensed health care provider, a clinical trial investigator, a medical record administrator, a clinical trial data record administrator, a site management organization, a contract research organization, a clinical trial administrator, a clinical trial monitor, a regulatory agency, a clinical trial sponsor, and an institutional or ethical review board, each of whom is capable of variably and selectively assuming a plurality of roles, including the roles of the other access and permissions managers; defining a plurality of roles associated with said plurality of access and permissions managers; defining a plurality of access and permissions sets for said plurality of roles of the access and permissions managers; and associating the assignments of the plurality of roles to the plurality of access and permissions managers; variably and selectively defining the assignments of the plurality of roles to the access and permissions managers, and the plurality of access and permissions sets for the plurality of roles of the access and permissions managers;

a database, wherein said database further comprises data tables that contain fields defined for receiving and storing medical record data or medical clinical trial data, and patient data associated therewith; and a second electronic processing device disposed in communication with said first electronic processing device, said software package and said database, said second electronic processing device further comprising a graphical user interface that displays a plurality of defined data fields associated with corresponding data fields defined within the database, wherein access to said plurality of defined data fields displayed in said graphical user interface, and therefore to corresponding data fields defined within said database, is controlled by said plurality of access and permissions managers variably and selectively providing and restricting access to said plurality of defined data fields in response to the setting of associated access and password restrictions controlled by said plurality of access and permissions managers.

2. The system of claim 1, wherein said users of the system are selected from a user selection set comprising a physician, a licensed health care provider, a clinical trial investigator, a medical record or clinical trial data record site management organization, a contract research organization, a clinical trial administrator, a clinical trial monitor, a regulatory agency, a clinical trial sponsor, and an institutional or ethical review board.

3. The system of claim 1, further comprising:

means for defining parameters of medical record data or medical clinical trial data and parameters of patient data associated therewith, and for storing said medical record data or said medical clinical trial data parameters and said data parameters associated therewith within the electronic source document;

means for defining requirements of medical record data requirements or medical clinical trial data and requirements of patient data associated therewith, and for storing said medical record data requirements or said medical clinical trial data requirements and said data requirements relating to the medical records or medical clinical trial within the electronic source document; and means for defining data types relating to medical records or medical clinical trials, and types of patient data associated therewith, and for storing said medical record or medical clinical trial data types and said data types associated therewith within the electronic source document.

4. The system of claim 1, wherein said access to said plurality of data fields defined within the database is subject to the control of the plurality of access and permissions control managers granting access and permission to write data in fields displayed in said graphical user interface.

5. The system of claim 2, further comprising means for said one or more users to amend said medical record data or said medical clinical trial data and patient data associated therewith stored in said electronic source document.

6. The system of claim 5, further comprising means for creating and maintaining an audit trail when said one or more of users amends medical record data or medical clinical trial data or patient data associated therewith stored in said electronic source document.

7. The system of claim 1, further comprising an application specific navigation tool.

8. The system claim 1, further comprising an Internet web browser, wherein said browser is disposed in communication with said electronic source document by means of one or more of an Internet connection, an Ethernet connection, a Bluetooth connection, an 802.11g connection, a wireless cellular connection, a hard wired computer terminal connection, a voice recognition or touch activated screen, a personal digital assistant, and a portable data management device.

9. A method of recording and sharing medical record data or data associated with a medical clinical trial and patient data associated therewith in a manner that creates and preserves an electronic record of stored original data so that a verifiable electronic source document is created and preserved, said method comprising:

disposing a first electronic processing device in communication with a software package that is capable of variably and selectively defining a plurality of access and permissions managers selected from medical care and clinical trials principals in an access and permissions manager selection set comprising a physician, a licensed health care provider, a clinical trial investigator, a medical record administrator, a clinical trial data record administrator, a site management organization, a contract research organization, a clinical trial administrator, a clinical trial monitor, a regulatory agency, a clinical trial sponsor, and an institutional or ethical review board, each of whom is capable of variably and selectively assuming a plurality of roles, including the roles of the other access and permissions managers; defining a plurality of roles associated with said plurality of access and permissions managers; defining a plurality of access and permissions sets for said plurality of roles of the access and permissions managers; and associating the assignments of the plurality of roles to the plurality of access and permissions managers; variably and selectively defining the assignments of the plurality of roles to the access and permissions managers, and the plurality of access and permissions sets for the plurality of roles of the access and permissions managers; and disposing a second electronic processing device in communication with said software package and said database, said second electronic processing device further comprising a graphical user interface that displays a plurality of defined data fields associated with corresponding fields defined within the database, wherein access to said plurality of defined data fields displayed in said graphical user interface, and therefore to corresponding data fields stored within the database, is controlled by a said plurality of access and permissions managers variably and selectively providing and restricting access to said plurality of data fields defined in said database in response to the setting of associated access and password restrictions controlled by said plurality of data managers.

10. The method of claim 9, further comprising: selecting one or more users of the system from a selection set comprising one or more of a clinical trial a physician, a licensed health care provider, a clinical trial investigator, a medical record or clinical trial data record site management organization, a contract research organization, a clinical trial administrator, a clinical trial monitor, a regulatory agency, a clinical trial sponsor, and an institutional or ethical review board.

11. The method of claim 9, further comprising:

defining parameters of medical record data or medical clinical trial data and parameters of patient data associated therewith, and then storing said parameters within the electronic source document;

defining requirements of medical record data or medical clinical trial data and requirements of patient data associated therewith, and then storing said requirements within the electronic source document; and defining data types relating to medical record data or medical clinical trial data, and types of patient data associated therewith, and then storing said data types within the electronic source document.

12. The method of claim 11, further comprising:

allowing access to said plurality of data fields defined within said database subject to said plurality of access and permissions managers granting permission to write data in fields displayed in said graphical user interface.

13. The method of claim 9, further comprising:

providing a means for said one or more users to amend said medical record data or said medical clinical trial data and said patient data associated therewith relating stored in said electronic source document.

14. The method of claim 13, further comprising:

providing a means for creating and maintaining an audit trail when said one or more of users amends said medical record data or said medical clinical trial data and said patient data associated therewith stored within said electronic source document.

15. The method of claim 9, further comprising: providing an application specific navigation tool.

16. The method claim 9, further comprising: disposing an Internet web browser in communication with said electronic source document by means of one or more of an Internet connection, an Ethernet connection, a Bluetooth connection, an 802.11g connection, a wireless cellular connection, a hard wired computer terminal connection, a voice recognition or touch activated screen, a personal digital assistant, and a portable data management device.

* * * * *